United States Patent [19]

Leung et al.

[11] Patent Number: 4,935,547

[45] Date of Patent: Jun. 19, 1990

[54] HOMOLOGATION PROCESS MAKING HIGHER ALCOHOLS

[75] Inventors: Tak W. Leung; Bernard D. Dombek, both of Charleston, W. Va.

[73] Assignee: Union Carbide Chemicals and Plastics Company Inc., Danbury, Conn.

[21] Appl. No.: 234,270

[22] Filed: Aug. 19, 1988

[51] Int. Cl.$^5$ .................. C07C 31/08; C07C 29/16
[52] U.S. Cl. ........................... 568/902.2; 518/700; 518/701; 568/902 H
[58] Field of Search .................. 518/700, 701; 568/902 H, 902.2

[56] References Cited

U.S. PATENT DOCUMENTS

| | | |
|---|---|---|
| 4,239,924 | 12/1980 | Pretzer et al. .............. 568/902.2 |
| 4,366,259 | 12/1982 | Knifton et al. .............. 518/700 |
| 4,374,285 | 2/1983 | Lin et al. .............. 568/902.2 |
| 4,391,919 | 7/1983 | Burdett .............. 518/700 |
| 4,434,247 | 2/1984 | Dombek .............. 518/700 |
| 4,436,837 | 3/1984 | Lin .............. 518/700 |
| 4,460,709 | 7/1984 | Kiso et al. .............. 518/700 |
| 4,590,216 | 5/1986 | Dombek .............. 518/700 |
| 4,592,870 | 6/1986 | Dombek .............. 260/410.6 |
| 4,605,677 | 8/1986 | Krifton .............. 518/700 |
| 4,618,628 | 10/1986 | Head et al. .............. 518/700 |

FOREIGN PATENT DOCUMENTS

| | | | |
|---|---|---|---|
| 0013008 | 6/1985 | European Pat. Off. . | |
| 48980 | 7/1985 | European Pat. Off. . | |
| 2571719 | 4/1986 | France .............. | 568/902 |
| 58-079940 | 5/1983 | Japan .............. | 518/700 |
| 59-190936 | 1/1984 | Japan . | |
| 59-73532 | 4/1984 | Japan . | |

OTHER PUBLICATIONS

Kiso et al., "Activation Effects of Imidazoles on Ruthenium Carbonyl-Halide Catalysts in Ethylene Glycol Formation From Syn Gas", J. of Organomet. Chem. 1986, 303 C17.

Kiso et al., "Effect of Imidazole on ruthenium Catalysts in Hydrogenation of Carbon Monoxide", New Cat. for Ethylene Glycol Synthesis, J. of Organomet. Chem. 1986, 309, C26.

Dombek, Organometallics, 1985, 4, 1707–1712.

Primary Examiner—Howard T. Mars
Attorney, Agent, or Firm—Reynold J. Finnegan

[57] ABSTRACT

A liquid phase process for the manufacture of $C_{2+}$ alkanols by the reaction of hydrogen with carbon monoxide in the presence of a catalyst containing ruthenium, cobalt, a halide-containing compound, and an aromatic compound substituted in adjacent ring positions by nitrogen atoms. The process embraces the use of rhodium as an additive to the catalyst system.

7 Claims, No Drawings

HOMOLOGATION PROCESS MAKING HIGHER ALCOHOLS

BACKGROUND TO THE INVENTION

The Government of the United States of American has rights in this invention pursuant to Contract No. DE-AC22-84PC70022 and DE-AC22-86PC90013 awarded by the U.S. Department of Energy.

BRIEF DESCRIPTION OF THE INVENTION

A liquid phase process for the manufacture of $C_{2+}$ alkanols by the reaction of hydrogen with carbon monoxide in the presence of a catalyst containing ruthenium, cobalt, a halide-containing compound, and an aromatic compound substituted in adjacent (viz. 1,2-) ring positions by nitrogen atoms. The process embraces the use of rhodium as an additive to the catalyst system. More particularly, the liquid phase process involves the manufacture of $C_{2+}$ alkanols by the reaction of hydrogen with carbon monoxide in the presence of a lower alkanol and a catalyst containing ruthenium, cobalt, a halide-containing compound, and an aromatic compound substituted in adjacent (viz. 1,2-) ring positions by nitrogen atoms at a pressure of about 500 pounds per square inch to about 20,000 pounds per square inch and at a temperature of about 100° C. to about 450° C. Preferably, the lower alkanol is produced in situ directly from the reaction of hydrogen with carbon monoxide.

The addition of methanol to gasoline as an octane improver and fuel extender is well known. It is also known that higher alcohols are desirable in such a fuel mixture to prevent moisture-induced phase separation of the methanol. These higher alcohols can be produced by known and established chemical processes, but it would be desirable to be able to co-produce them with methanol from synthesis gas ("syngas"), i.e., mixtures of carbon monoxide and hydrogen. Described here are catalytic processes which allow the practical formation from syngas of mixtures of methanol and higher alcohols for direct addition to gasoline.

Soluble ruthenium complexes have been reported to be active catalysts for the conversion of syngas to alchols. Amines were reported to be promoters for the ruthenium carbonyl complexes in the production of alcohols and ethylene glycol, but they do little to increase the production of $C_{2+}$ alcohols. (See B. D. Dombek, European Patent Appl. No. 13008), o-Phenylenediamine (1,2-phenylenediamine) was reported to promote the activity of ruthenium carbonyl complex catalysts in a process for producing methanol and ethylene glycol, but the process yielded insignificant amounts of $C_{2+}$ alcohols (S. Nakamura, T. Deguchi, T. Takano and M. Ishino, Jap. Pat. JP 59/73532). A derivative of o-phenylenediamine, benzimidazole, was also reported in the literature (Kiso, Y.; Saeki, K. Japanese Pat. JP 58/22503 A2; idem. J. Organomet. Chem. 1986, 303, C17 and idem. ibid. 1986, 309, C26), again to promote the activity of the ruthenium system to produce methanol and ethylene glycol but not $C_{2+}$ alcohols.

Halides were reported to be a promoter for the ruthenium system which increases both the activity and selectivity to $C_{2+}$ alcohols (B. D. Dombek, Eur. Pat. Pub. 48980.

Bimetallic systems containing ruthenium and another metal were reported to be more active and/or more selective in producing certain products. Catalyst systems containing ruthenium, samarium or another rare earth element, and halides were reported to produce more $C_{2+}$ alcohols than the system without samarium or the other rare earth elements (B. D. Dombek, U.S. Pat. No. 4,590,216 and J. J. Lin, U.S. Pat. No. 4,436,837).

Catalyst systems containing ruthenium, rhodium and halides were shown to produce proportionally more ethylene glycol (B. D. Dombek, P. W. Hart, and G. L. O'Connor, European Patent Publication 84682, published Aug. 3, 1983).

Catalyst systems which contain ruthenium and cobalt have been reported to increase the yield of $C_{2+}$ products, but the products are in the form of acetic acid or acetates, and the yield to alcohols is poor. In fact, the patent by Knifton and Lin (U.S. Pat. No. 4,366,259) claimed that the catalyst systems containing ruthenium and cobalt dispersed in a molten phosphonium salt convert syngas to acetic acid selectively. Nevertheless, this reported bimetallic system, besides not being one that produces $C_{2+}$ alcohols, did not show much improvement on the activity over the system using ruthenium alone.

Similar results were obtained in a Japanese patent (see JP 59/190935) which claimed the use of ruthenium, cobalt and halides as catalysts using phosphoric acid as solvent. Catalyst systems similar to those in the Japanese patent were also reported by R. A. Head and R. Whyman (U.S. Pat. No. 4,618,628) to convert syngas directly to higher alcohols, but those systems require a much higher pressure (12,500 psi) to obtain a rate equivalents to about 1.0M/h to alcohols. Also, it is not clear from their patent how much acetic acid and acetates, which are less desirable products, were present in the product of their experiments.

There are many patents which claims the use of ruthenium and cobalt as catalyst systems for the conversion of methanol and syngas to ethanol. However, none disclose the use of catalyst containing ruthenium, cobalt, a halide-containing compound, and an aromatic compound substituted in adjacent (e.g., 1,2-) ring positions by nitrogen atoms.

THE INVENTION

The invention relates to a liquid phase process for the manufacture of $C_{2+}$ alkanols by the reaction of hydrogen with carbon monoxide in the presence of a catalyst containing ruthenium, cobalt, a halide-containing compound, and an aromatic compound substituted in adjacent (viz., 1,2-) ring positions by nitrogen atoms. More particularly, the invention relates to a liquid phase process for the manufacture of $C_{2+}$ alkanols by the reaction of hydrogen with carbon monoxide in the presence of a lower alkanol and a catalyst system containing ruthenium, cobalt, a halide-containing compound, and an aromatic compound substituted in adjacent (such as 1,2-) ring positions by nitrogen atoms at a pressure of about 500 pounds per square inch to about 20,000 pounds per square inch and at a temperature of about 100° C. to about 450° C.

In a preferred embodiment of the process of the invention, the lower alkanol is produced in situ directly from the reaction of hydrogen with carbon monoxide in the course of producing the $C_{2+}$ alkanols.

In another preferred embodiment of the process of the invention, the nitrogen atoms substituted on the aromatic compound are amino groups or comprise part of an imidazole ring structure.

In a further embodiment of the invention, rhodium is provided in the catalyst system to enhance the formation of $C_{3+}$ alkanols.

DETAILS OF THE INVENTION

The invention relates to the use of catalyst systems containing a ruthenium, cobalt, halide and an ortho nitrogen di-substituted aromatic compound. In an optional embodiment, the invention encompasses the use in the catalyst system of a catalytic amount of rhodium. The invention also relates to the use of these catalyst systems to effectively convert syngas directly to alcohols and the homologation of alcohols to higher molecular weight alcohols. The catalyst systems of the invention produce alcohols selectively and very little undesirable products such as formates and acetates are produced. The catalyst systems of the invention produce a substantially higher proportion of $C_{2+}$ alcohols than other syngas to alcohol catalyst systems.

The process of the invention is primarily directed to the production of higher alcohols which in the context of the invention are alkanols containing 2 or more carbon atoms, for example, ethanol, propanol, isopropanol, the butanols, and the like. These higher alcohols have greater value measured in commercial terms than methanol, which in the context of the invention constitutes the lower alcohol. The invention embraces an effective process of homologating methanol to the higher alcohols. The invention also embraces an effective process of making methanol directly from syngas while simultaneously homologating some of the methanol so produced to higher alcohols, thereby conjointly producing the lower and the higher alcohols. The invention allows the incorporation to the catalyst system of rhodium thereby providing a process which generates enhanced amounts of $C_{3+}$ alcohols, such as the propanols, butanols, pentanols, and the other members of the homologous series.

The process of the invention relates to the use of a complex catalyst system which involves a variety of diverse components yet which conjointly operate to react syngas to form methanol and homologate methanol to form one or more of the $C_{2+}$ alkanols. The invention can also be used to homologate methanol to form the $C_{2+}$ alkanols.

The process of the invention typically comprises the formation of a homogeneous liquid phase mixture of the catalyst system and syngas. Any heterogeneous component present in the reaction mixture would generally be a precursor component waiting to be solubilized in the carrying out of the process by reaction with another component of the reaction system such as syngas or carbon monoxide.

The ruthenium component of the catalyst system of the invention may be any ruthenium compound which can be solubilized in the reaction medium. As a rule, the ruthenium catalysts are easily obtainable as soluble components and can be used in the form of non-volatile compounds possessing high thermal stability, and exhibiting high catalytic activity at elevated temperatures. From a practical standpoint, the physical and chemical properties of the ruthenium catalyst (soluble, nonvolatile, and possessing high thermal stability) permit product removal by distillation.

The selection of a suitable ruthenium compound to provide the catalytic activity for the homologation reaction and the direct reaction of syngas to alcohol is not narrowly critical. Essentially any ruthenium compound can be effectively employed to carry out these reactions. It is believed the primary requirement for the generation of such catalysts and the requisite catalytic activity are ruthenium precursors to the catalyst which can be converted to a ruthenium carbonyl complex. The process of this invention may be practiced with a vast array of ruthenium compounds. Even in instances where the ruthenium compound is too stable for catalyzing the reaction, catalysis can be effected by including a compound which does not adversely affect the syngas and homologation reactions and stimulates the ruthenium compound to be converted to a species having catalytic activity. For example, ruthenium chloride is a sluggish catalyst but is made quite active by the addition of an alkali such as an alkali metal salt of a carboxylic acid, viz. sodium acetate. It is not presumed that simple ruthenium salt compounds are the catalyst or that many of the ruthenium compounds herein used to effect the catalytic reaction are the catalyst. The exact ruthenium containing compound or compounds that constitute the catalyst of this invention is not appreciated but what is appreciated is that many ruthenium compounds can be used to in situ generate the catalyst. The diversity of the selection of ruthenium compounds suitably employable as precursors to catalysts in the process of the invention is quite broad; illustrative of this point—the precursor compounds may range from supported ruthenium such as ruthenium on carbon, alumina, and the like, to ruthenium carbonyl to ruthenium (III) acetylacetonate.

Under the conditions of the reaction, the ruthenium is present as a complex which contains carbon monoxide directly bonded to ruthenium (ruthenium carbonyl). The ruthenium compound which is provided to the reaction is not necessarily in a form which will effectively catalyze the reaction even if it contains a carbon monoxide ligand bonded to it. Ruthenium compounds such as ruthenium salts, oxides and carbonyl clusters may be introduced to the reaction in a condition which allows them to be solublized, and under the conditions of the reaction they are converted into a carbonyl complex which effectively catalyzes the reaction.

The composition and structure of the ruthenium carbonyl complex which catalyzes the desired reaction is not specifically known. It may be a monoruthenium or polyruthenium compound. Illustrative of polyruthenium compounds are the well-known cluster compounds of ruthenium. However, the addition of a cluster, containing only a carbonyl ligand such as $Ru_3(CO)_{12}$ does not alone create the catalyst and, as such, cause the catalytic reaction. Some modification of such structure is needed, possibly the destruction of the cluster structure to a mononuclear ruthenium structure. Factors to be considered in achieving the catalyst are the reaction parameters and the choice of solvent. Because varied reaction conditions and solvents, with and without promoters, result in different amounts of the desired products of the process, and different rates, efficiencies and/or yields, it is presumed that each provides a different and distinct catalytic environment.

The ruthenium-containing substances which may be employed in the practice of this invention to form the catalyst under process conditions encompass those which are described, for example, in Gresham, U.S. Pat. No. 2,535,060 at column 2, starting at line 38 to line 48, and ruthenium carbonyl compounds. It is not advisable to place ruthenium compounds or substances on a support material for use in the process of this invention because it offers no benefits over solubilizing such ruthenium compounds in combination with a solvent. Moreover, ruthenium deposited on a support material can be expected to be solubilized in the homogeneous liquid phase reaction system of this invention as it is contacted with carbon monoxide. Even ruthenium metal in the presence of the solvent, carbon monoxide and hydrogen can be converted to a ruthenium carbonyl complex which is soluble. Ruthenium oxides, such as dioxide, sesquioxide, or tetraoxide, are capable under appropriate conditions of being solubilized and converted to a carbonyl complex which can be used to form the catalyst under conditions of this process. However, when using such insoluble ruthenium compounds, they must first be solubilized before the effective operation of the process of this invention.

Ruthenium carbonyl compounds (which include ruthenium carbonyl hydrides or ruthenium carbonyl clusters) are already provided with a carbonyl ligand, and under the conditions of the reaction can be sufficiently changed to achieve the desired catalytic effect. Ruthenium salts such as those of organic acids can be employed in the practice of this invention to produce the catalyst. In addition to those ruthenium compounds described in the aforementioned Gresham patent, one may employ ruthenium compounds of bidentate ligands, allyl complexes, arene complexes, halides, and alkyl complexes. The choice of ruthenium compounds is varied and not critical to this invention. A number of ruthenium complexes are known to be more stable to the presence of carbon monoxide than other ruthenium compounds and the skilled worker can determine which particular ruthenium compound might take longer to initiate a reaction than other ruthenium compounds. On that basis, one can select for the purposes of convenience the particular ruthenium compound to be utilized in forming the catalyst. However, ruthenium which is associated with an organic molecule or complexed with carbon monoxide is most readily solubilized so as to provide the ruthenium catalyst of this process.

The ruthenium catalyst precursors may taken many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium-(III) chloride and ruthenium nitrate, or as the salt of a suitable organic carboxylic acid, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as tricarbonylruthenium(II) chloride dimer, $[Ru(CO)_3Cl_2]_2$.

The cobalt component of the catalyst system can be supplied from any number of sources, many of these are known to those of ordinary skill in the art. Thus, it is not necessary for an understanding thereof to specifically enumerate every suitable type and every specific compound since any of the known compounds can be used. Cobalt promotes the formation of higher alcohols in the presence of iodide and ortho nitrogen di-substituted aromatic compound. It is generally believed that the effective form of the cobalt compound comprises cobalt carbonyl; however, the direct charging of a cobalt carbonyl complex to the reaction medium is not required. Nevertheless, descriptive of some of the useful cobalt sources are the known cobalt carboxylates such as cobalt formate, cobalt acetate, cobalt benzoate, cobalt toluate, cobalt propionate, cobalt butyrate, cobalt valerate, cobalt hexanoate, cobalt cyclohexylbutyrate, and the like; the cobalt carbonyls such as dicobalt octacarbonyl, acetyl cobalt tetracarbonyl, tricobalt dodecacarbonyl, and the like, including their phosphine substituted analogs many of which are known to those skilled in the art; the cobalt oxides such as cobalt oxide; cobalt hydroxide, cobalt halides such as cobalt iodide; cobalt carbonate; cobalt bicarbonate; cobalt. Any of the known cobalt complexes can also be used. Mixtures of cobalt compounds can be used. For example, the charging of any cobalt (II) compound which can be converted in situ into dicobalt octacarbonyl and/or cobalt hydrocarbonyl under the reaction conditions employed and which causes no adverse side effects is sufficient. Various other cobalt carbonyl species in addition to those named may be produced under the reaction conditions, and may, in whole or in part, be effective catalyst system components. All such species are referred to herein as "cobalt carbonyl".

The presence of a halide in the reaction is essential for the production of higher alcohols. The halide component of the catalyst system of the invention may be supplied as a halogen compound such as hydrogen halide, alkyl- or aryl-halide, metal halide, ammonium, phosphonium, arsonium and stibonium halide, and may be the same or different from any halogen component provided in the Ru, Co or aromatic compound substituted in adjacent (viz., 1,2-) ring positions by nitrogen atoms that are components of the catalyst system. Halogen or halide compounds are generally suitable for the catalyst system, but those containing iodine and bromine are preferred, with hydrogen iodide constituting a more preferred member. Accordingly, suitable compounds providing the halide component of the catalyst system of this invention may be selected from the following list of preferred halogen and/or halogen containing compounds:

$RX_n$ where n is 1 to 3, X is one of Cl, Br and I, R may be any alkyl, alkylene or aryl group, thereby embracing compounds such as, e.g., $CH_3I$, $C_2H_5Br$, $CH_3CH_2I$, $ICH_2CH_2I$, and the like;

$X_2$ or $X^-$ where X is one of Cl, Br, and I, thereby embracing molecules and ions as, e.g., $Br_2$, $I_2$, $I^-$,

HX where X is one of Cl, Br, and I, to provide such compounds as, e.g., HBr and HI.

AlkX where X is one of Cl, Br, and I, Alk is an alkali or alkaline earth metal such as Li, Na, K, Rb, Cs, Ca, Mg, Be, Sr, and Ba to provide such compounds as, e.g., LiBr, KI and $MgI_2$.

RC(O)X where X is one of Cl, Br, and I, and R may be any alkyl, alkenyl or aryl-groups, to provide such compounds as, e.g., $CH_3(O)I$, and the like;

$R'_aMX$, $R'_bMX_2$, or $R'_cMX_3$ where X is one of Cl, Br and I, R' is one or more of hydrogen or any alkyl- or aryl-group, M is one of N, P, As and Sb, and a, b and c represent the free valence of M, to provide such compounds as, e.g., $NH_4I$, $PH_4I$, $PH_3I_2$, $PH_3Br_2$, $(C_6H_5)_3PI_2$, and other combinations of R, M and X.

Variations in the selection of halide can have a more beneficial effect on the process of the invention. Some halides are more effective in the production of higher alcohols generally and some are more effective in producting $C_{3+}$ alcohols specifically. For example, tetrabutylphosphonium bromide has been shown in some catalyst systems encompassed by the invention to be more effective than, e.g., KI and LiI, in producing $C_{3+}$ alcohols.

The catalytic activity and selectivity to the higher alcohols is enhanced by providing the nitrogen substituted aromatic compound to the catalyst system of the invention. The combination of the nitrogen substituted aromatic compound and the halide component have been found essential for increasing the activity and selectivity of the catalyst system to generate higher alcohols from syngas. The aromatic compound substituted in adjacent ring positions by nitrogen atoms may be any aromatic structure soluble in the reaction medium which possesses the structure

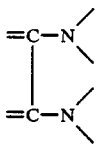

wherein the carbon atoms form part of an aromatic ring and the double bonds represent aromatic unsaturation, and the nitrogen and its free valences constitute part of any group capable of forming an imidazole ring structure under the conditions of the syngas and homologation reactions or constitute part of an imidazole ring structure. The aromatic component of the compound may be a single or multiple ring structure. It may contain halide, alkyl, aryl, alkoxy, aroxy, and the like substitution. Apart from the fact that the aromatic compound requires the adjacent ring positioning of the nitrogen atoms, there are essentially no other limitations in structures considered important to the selection of the compound.

Simple illustrations of such nitrogen substituted aromatic compounds are ortho (o) phenylenediamine and the substituted o-phenylenediamines. Illustrative of the latter are o-phenylenediamines in which one to four hydrogen atoms on the benzene ring are substituted with groups such as halo, alkyl, cycloalkyl, aryl, aralkyl, alkoxy, hydroxy, carboxyl, amino, and nitro groups, and the remaining ring carbon atoms are bonded to hydrogen atoms. Preferred among these substituted o-phenylenediamines are compounds in which one to four hydrogen atoms on the benzene ring are substituted with alkyl groups.

Specific examples of preferred phenylenediamines include o-phenylenediamine, tolylene-3,4-diamine, 4,5-dimethyl-o-phenylenediamine, and 2,3-diaminonaphthalene.

As pointed out above, rhodium may be added to the catalyst system of the invention to enhance the production of $C_{3+}$ alkanols. The rhodium component of the catalyst system of the invention may be any rhodium compound which can be solubilized in the reaction medium. As a rule, the rhodium component is easily obtainable as a soluble component and can be used in the form of non-volatile compounds possessing high thermal stability, and exhibiting high catalytic activity at elevated temperatures in the catalyst system for enhancing the production of $C_{3+}$ alcohols.

Essentially any rhodium compound can be effectively employed to enhance higher alcohol production. It is believed the primary requirement for the requisite catalytic activity of the rhodium component are rhodium precursors to the catalyst which can be converted to a rhodium carbonyl complex compounds. The process of this invention may be practiced with a vast array of rhodium compounds. Even in instances where the rhodium compound is too stable for catalyzing the reaction, catalysis can be effected by including a compound which does not adversely affect the syngas and homologation reactions and stimulates the rhodium compound to be converted to a species having catalytic activity. For example, rhodium chloride is a sluggish catalyst but is made quite active by the addition of an alkali such as an alkali metal salt of a carboxylic acid, viz. sodium acetate. It is not presumed that simple rhodium salt compounds are the catalyst or that many of the rhodium compounds herein used to effect the catalytic reaction are the catalyst. The exact rhodium containing compound or compounds that constitute the catalyst of this invention is not appreciated but what is appreciated is that many rhodium compounds can be used to in situ generate the catalyst. The diversity of the selection of rhodium compounds suitably employable as precursors to catalysts in the process of the invention is quite broad.

Under the conditions of the reaction, the rhodium is present as a complex which contains carbon monoxide directly bonded to rhodium (rhodium carbonyl). The rhodium compound which is provided to the reaction is not necessarily in a form which will effectively catalyze the reaction even if it contains a carbon monoxide ligand bonded to it. Rhodium compounds such as rhodium salts, oxides and carbonyl clusters may be introduced to the reaction in a condition which allows them to be solubilized, and under the conditions of the reaction they are converted into a carbonyl complex which effectively catalyzes the reaction.

The composition and structure of the rhodium carbonyl complex which catalyzes the desired reaction is not specifically known. It may be a monorhodium or polyrhodium compound. Illustrative of polyrhodium compounds are the well-known cluster compounds of rhodium. However, the addition of a cluster, containing only a carbonyl ligand such as $Rh_4(CO)_{12}$ does not alone create the catalyst and, as such, cause the catalytic reaction. Some modificatiin of such structure is needed, possibly the destruction of the cluster structure to a mononuclear rhodium structure. Factors to be considered in achieving the catalyst are the reaction parameters and the choice of solvent. Because varied reaction conditions and solvents, with and without promoters, result in different amounts of the desired products of the process, and different rates, efficiencies and/or yields, it is presumed that each provides a different and distinct catalytic environment.

The rhodium-containing substances which may be employed in the practice of this invention to form the catalyst under process conditions encompass those which are described, for example, in Pruett et al., U.S. No. 3,833,634, patented Sept. 3, 1974, illustrative of this point—the precursor compounds may range from supported rhodium such as rhodium on carbon, alumina, and the like, to rhodium carbonyl to chloro(1,5-cyclooctadiene)rhodium (I) dimer. It is not advisable to place rhodium compounds or substances on a support material for use in the process of this invention because it offers no benefits over solubilizing such rhodium compounds in combination with a solvent. Moreover, rhodium deposited on a support material can be expected to be solubilized in the homogeneous liquid phase reaction system of this invention as it is contacted with carbon monoxide. Even rhodium metal in the presence of the solvent, carbon monoxide and hydrogen can be converted to a rhodium carbonyl complex which is soluble. Rhodium oxides, such as dioxide, sesquioxide, or tetraoxide, are capable under appropriate conditions of being solubilized and converted to a carbonyl complex which can be used to form the catalyst under conditions of this process. However, when using such insoluble rhodium compounds, they must first be solubilized before they are effective in contributing to the process of this invention.

Rhodium carbonyl compounds (which include rhodium carbonyl hydrides or rhodium carbonyl clusters) are already provided with a carbonyl ligand, and under the conditions of the reaction can be sufficiently changed to achieve the desired catalytic effect. Rhodium salts such as those of organic acids can be employed in the practice of this invention to produce the catalyst. In addition to those rhodium compounds described in the aforementioned Pruett, et al., one may employ rhodium compounds of bidentate ligands, allyl complexes, arene complexes, halides, and alkyl complexes. The choice of rhodium compounds is varied and not critical to this invention. A number of rhodium complexes are known to be more stable to the presence of carbon monoxide than other rhodium compounds and the skilled worker can determine which particular rhodium compound might take longer to initiate a reaction than other rhodium compounds. On that basis, one can select for the purposes of convenience the particular rhodium compound to be utilized in forming the catalyst. However, rhodium which is associated with an organic molecule or complexed with carbon monoxide is most readily solubilized so as to provide the rhodium catalyst of this process.

The rhodium catalyst precursors may taken many different forms. For instance, the rhodium may be added to the reaction mixture in an oxide form, as in the case of for example, rhodium(IV) oxide hydrate, anhydrous rhodium(IV) dioxide and rhodium(III) oxide. Alternatively, it may be added as the salt of a mineral acid, as in the case of rhodium(III) chloride hydrate, rhodium(III) bromide, rhodium(III) iodide, tricarbonyl rhodium(II) iodide, anhydrous rhodium(III) chloride and rhodium nitrate, or as the salt of a suitable organic carboxylic acid, for example, rhodium(III) acetate, rhodium naphthenate, rhodium valerate and rhodium complexes with carbonyl-containing ligands, such as rhodium(III) acetylacetonate. The rhodium may also be added to the reaction zone as a carbonyl or hydrocarbonyl derivative. Here, suitable examples include tetrarhodium dodecacarbonyl and hexarhodium hexadecacarbonyl, and substituted carbonyl species such as chlorodicarbonylrhodium (I) dimer, $[RhCl(CO)_2]_2$.

Under some conditions, the addition of the rhodium component to the reaction results in a loss of catalytic activity. This loss can be effectively overcome by increasing the amount of the nitrogen substituted aromatic compounds in the reaction medium, hence the catalyst system.

The quantity of ruthenium catalyst employed is not narrowly critical and can vary over a wide range. In general, the process is desirably conducted in the presence of a catalytically effective quantity of the active ruthenium species which gives a suitable and reasonable reaction rate. Reaction can proceed when employing as little as about $1 \times 10^{-6}$ weight percent, and even lesser amounts, of ruthenium based on the total weight of reaction mixture (i.e., the liquid reaction mixture). The upper concentration limit can be quite high, e.g., about 30 weight percent ruthenium, and higher, and the realistic upper limit in practicing the invention appears to be dictated and controlled by economics in view of the cost of ruthenium. Since the rate of conversion of syngas may be dependent upon the concentration of ruthenium employed, higher concentrations achieving higher rates, then large concentrations may prove to be a most desirable embodiment of this invention. Depending on various factors such as the promoter concentrations, the partial pressures of syngas, the total operative pressure of the reaction system, the operative temperature, the choice of solvent if one is employed, and other considerations, a catalyst concentration of about $1 \times 10^{-3}$ to about 20 weight percent ruthenium (contained in the complexed catalyst) based on the total weight of the reaction mixture, is generally acceptable in the practice of the invention.

The amounts of the cobalt, halide ion and ortho disubstituted aromatic nitrogen compound will be sufficient to promote the reaction of the higher alcohols. As used herein, higher alcohols mean those alcohols having at least 2 carbon atoms. Methanol is a lower alcohol. The ratios of ruthenium to cobalt to halide to ortho aromatic nitrogen compound to rhodium used in the practice of the process of the invention, may range from about 0.001 mole to about 1 mole of Ru: about 0.001 mole to about 1 mole of Co: about 0.001 mole to about 1 mole of halide (halide ion content): about 0.1 mole to about 10,000 moles, preferably about 10 to about 1,000 moles, of the ortho di-substituted aromatic nitrogen compound; and 0 mole to about 1 mole of rhodium.

The present reaction is carried out in an atmosphere of carbon monoxide and hydrogen. $H_2/CO$ mole ratio of the syngas provided to the reaction may range from about 0.1:1.0 to about 10:1.0, most preferably 0.2:1.0 to 5:1.0. Often it will be convenient to use approximately equimolar ratios, or whatever ratios are conveniently available in synthesis gas. The reaction to produce ethanol preferably utilizes 2 moles hydrogen per mole of carbon monoxide, but it is not necessary to have the reactants present in stoichiometric ratio. The carbon monoxide contributes to catalyst stability and appreciable carbon monoxide pressuree is therefore generally used such as about 500 psi to about 20,000 psi or more, and preferably the reaction is carried out under a total pressure of at least about 1,000 to about 15,000 psi, and often conveniently at about 2000 to about 5000 psi. The sum of the carbon monoxide and hydrogen pressures often constitute approximately the total pressure, and the aforesaid ranges apply to this sum.

The temperature at which the reaction is conducted may be as low as about 100° C. to about 400° C. The more preferable temperature may range from about 180° C. to about 260° C.

The catalytic reaction can be operated with or without a liquid solvent. When a liquid solvent is used, the solvent can be any organic compound, such as saturated or unsaturated hydrocarbon, alcohols, acetates, ethers, acids, amines, or low-melting ammonium or phosphonium salts, etc. The catalyst can operate without a solvent because o-phenylenediamine is a low-melting solid and can function as a solvent itself when melted.

The process is effected for a perod of time sufficient to produce the desired alcohol products. In general, the residence time to produce the desired products can vary from minutes to a number of hours, e.g., from a few minutes to 24 hours, and longer. It is readily appreciated that the residence period (time) will be influenced to a significant extent by the reaction temperature, the concentration and choice of promoters, ruthenium source, the total gas pressure and the partial pressure exerted by its components, the concentration and choice of solvent, and other factors. The synthesis of the desired product(s) by the reaction of hydrogen with carbon monoxide is suitably conducted under operative conditions which give reasonable reaction rates and/or conversions.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be lifted with internal and/or external heat exchanger(s) to thus control undue temperature fluctuations, or to prevent any possible "runaway" reaction temperature due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art.

The catalyst system may be initially introduced into the reaction zone batchwise, or it may be continuously or intermittently introduced into such zones during the course of the synthesis reaction. Means to introduce and/or adjust the reactants, either intermittently or continuously, into the reaction zone during the course of the reaction can be conveniently utilized in the process especially to maintain the desired molar ratios of, and the partial pressures exerted by, the reactants.

As intimated previously, the operative conditions can be adjusted to optimize the conversion of the desired product and/or the economics of the process. In a continuous process, for instance, when it is preferred to operate at relatively low conversions, it is generally desirable to recirculate unreacted synthesis gas with or without make-up carbon monoxide and hydrogen to the reactor. In addition, methanol or higher alcohols formed by the process can be recycled or maintained in the reactor so as to homologate them to higher boiling alcohols. Recovery of the desired product can be achieved by methods well-known in the art such as by distillation, fractionation, extraction, and the like. A fraction comprising catalyst complex, generally contained in by products and/or the solvent, can be recycled to the reaction zone, if desired. All or a portion of such fraction can be removed for recovery of the catalyst system components values or regeneration thereof, if necessary. Fresh catalyst components and/or solvent, can be intermittently added to the recycle stream or directly to the reaction zone, if needed.

EXAMPLE 1

A catalyst system containing 4.7 mmoles of $Ru_3(CO)_{12}$, 7.0 mmoles of $Co_2(CO)_8$, 30 mmoles of KI, and 92 mmoles of o-phenylenediamine was charged to a 300 milliliters autoclave along with 37.5 milliliters of diphenyl ether. The autoclave was purged with nitrogen and then with oxygen. After it was pressurized with 1000 psi of 1:1 $CO/H_2$ syngas, the autoclave was heated to the reaction temperature of 230° C. The pressure was then increased to 5000 psi, and it was kept within ±200 psi of 5000 psi by periodically repressurizing the system as gas uptake took place. After 3.0 hours, the system was cooled rapidly by a cooling coil to room temperature. After releasing the pressure, the liquid was analyzed by gas chromatography and shown to contain 12.7 grams (397 mmole) of methanol, 6.45 grams (140 mmole) of ethanol, 0.48 gram (8 mmole) n-propanol, 0.1 gram (1 mmole) of n-butanol, 0.55 gram (9 mmole) ethylene glycol, and 0.25 gram (4 mmole) of methyl acetate. The average rate to total liquid products was 5.0 moles/hour. Selectivity to alcohols was 98% by mole determination.

EXAMPLE 2

An experiment using the same catalyst system as in example 1 but using 45 milliliters of tetrahydrofuran as solvent in place of diphenyl ether was carried out according to the procedure described in example 1. GC analysis showed the formation of 11.2 grams (350 mmoles) of methanol, 5.0 grams (109 mmoles) of ethanol, 0.3 gram (5 mmoles) of n-propanol, 0.1 gram (1 mmole) of methyl acetate, and 0.5 gram (8 mmoles) of ethylene glycol.

EXAMPLE 3

An experiment using the same catalyst system as in example 1 but using 35 milliliters of sulfolane as solvent in place of diphenyl ether was carried out according to the procedure described in example 1 with a reaction time of 2.0 hours. GC analysis showed the formation of 2.4 grams (75 mmoles) of methanol, 4.6 grams (100 mmole) of ethanol, 0.7 gram (12 mmoles) of n-propanol, and 0.1 gram (1 mmole) of methyl acetate.

EXAMPLE 4

An experiment using the same catalyst as in example 1 but using 45 milliliters of ethanol as solvent in place of diphenyl ether was carried out according to the procedure described in example 1. GC analysis showed the formation of 11.5 grams (359 mmoles) of methanol, 3.6 grams (78 mmoles) of ethanol (net gain), 2.12 gram (35 mmoles) of n-propanol, and 0.35 gram (5 mmoles) of n-butanol.

EXAMPLE 5

An experiment using the same catalyst system as in example 1 but using 45 milliliters of methanol as solvent in place of diphenyl ether was carried out according to procedure described in example 1. GC analysis showed a loss of 5.0 grams (156 mmoles) of methanol and the formation of 11.4 grams (247 mmoles of ethanol, 1.2 gram (20 mmoles) of propanol, 0.2 gram (3 mmoles) of n-butanol and 0.4 gram (5 mmoles) of methyl acetate.

EXAMPLE 6

An experiment using the same catalyst system and solvent as in example 1 was carried out according to the procedure described in example 1 except using 4000 psi as the maximum pressure. GC analysis showed the formation of 8.4 grams (263 mmoles) of methanol, 4.3 grams (94 mmoles) of ethanol, 0.3 gram of n-propanol (5 mmoles) and 0.1 gram (1 mmole) of methyl acetate.

EXAMPLE 7

An experiment using the same catalyst system and solvent as in example 1 was carried out according to the procedure described in example 1 except using 3000 psi as the maximum pressure. GC analysis showed the formation of 4.7 grams (147 mmoles) of methanol, 0.64 gram (139 mmoles) of ethanol, and 0.1 gram (1 mmole) of methyl acetate.

EXAMPLE 8

An experiment using the same catalyst system and solvent as in example 1 was carried out according to the procedure described in example 1 except using 2000 psi as the maximum pressure. GC analysis showed the formation of 2.4 grams (75 mmoles) of methanol, 0.1 gram (2 mmoles) of ethanol and 0.1 gram (1 mmole) of methyl acetate.

EXAMPLE 9

An experiment using the same catalyst system as in example 1 and using the solvent THF was carried out according to the procedure described in example 1 except at an operating temperature of 245° C. GC analysis showed the product contained 9.9 grams (309 mmoles) of methanol, 6.0 grams (130 mmoles) of ethanol, 0.50 gram (8 mmoles) of n-propanol, 0.3 gram (4 mmoles) of n-butanol, 0.1 gram (1 mmole) of methyl acetate and 0.2 gram (3 mmoles) of ethylene glycol.

EXAMPLE 10

An experiment using the same catalyst system as in example 1 and using the solvent THF was carried out according to the procedure described in example 1 except at an operating temperature of 215° C. GC analysis showed the formation of 5.6 grams (175 mmoles) of methanol, 1.8 gram (39 mmoles) of ethanol, 0.2 gram (3 mmoles) of n-propanol, 0.2 gram (3 mmoles) of methyl acetate, 0.5 gram (8 mmoles) of ethylene glycol.

EXAMPLES 11–15

These examples demonstrate effects on the amounts of products formed using different solvents. The catalyst system contains 14 mmoles of Ru, 14 mmoles of Co, 93 mmoles of o-phenylenediamine, and 30 mmoles of KI in 40 grams of the solvent. Experiments were carried out at 5000 psi of 1:1 syngas, at 230° C. for 3.0 hours unless further specified.

TABLE 1

| Ex. | Solv. | MeOH | $C_{2+}$ROH | Other Ox[3] | % ROH | % $C_{2+}$ROH | Rate |
|---|---|---|---|---|---|---|---|
| 11 | Phenylether | 12.7 g | 7.1 g | 0.8 g | 96% | 35% | 5.0 M/h |
| 12 | THF | 11.2 g | 5.3 g | 0.6 g | 96% | 38% | 3.5 M/h |
| 13 | Sulfolane[1] | 2.4 g | 5.3 g | 0.1 g | 99% | 68% | 2.1 M/h |
| 14 | Ethanol | 11.5 g | 6.0 g[2] | 0.8 g | 96% | 33% | 3.3 M/h |
| 15 | Methanol | −5.0 g | 12.8 g | 0.4 g | 97%[4] | 97% | 0.8 M/h[5] |

[1]2.0 hours reaction time.
[2]net gain of ethanol.
[3]Other oxygenated liquid products.
[4]no net methanol formation
[5]rate directly from syngas only; Rate $C_{2+}$alcohols is 2.0 M/h.

EXAMPLES 16–19

These examples, 16–19, are taken from examples 1 and 6–8, respectively, to demonstrate the effect of different syngas pressures on the amount of alcohol product formed. As indicated previously, the catalyst system contained 14 mmoles of Ru, 14 mmoles of Co, 93 mmoles of o-phenylenediamine, and 30 mmoles of KI in 37.5 milliliters of diphenyl ether.

TABLE 2

| Example | Pressure | MeOH | $C_{2+}$ROH | Other Ox[6] | % ROH | % $C_{2+}$ROH | Rate Total |
|---|---|---|---|---|---|---|---|
| 16 | 5000 | 12.7 g | 7.1 g | 0.80 g | 96% | 35% | 5.0 M/h |
| 17 | 4000 | 8.4 g | 4.6 g | 0.1 g | 99% | 35% | 3.2 M/h |
| 18 | 3000 | 4.7 g | .64 g | 0.1 g | 98% | 12% | 1.4 M/h |
| 19 | 2000 | 2.4 g | 0.1 g | 0.1 g | 96% | 4% | 0.7 M/h |

[6]Other oxygenated liquid products.

EXAMPLES 20–22

These examples demonstrate the amount of products formed at different temperatures. The catalyst system contained 14 mmoles of Ru, 14 mmoles of Co, 93 mmoles of o-phenylenediamine, and 30 mmoles of KI in 45 milliliters of THF.

TABLE 3

| Example | Temperature | MeOH | $C_{2+}ROH$ | Other Ox[7] | % ROH | % $C_{2+}ROH$ | Rate Total |
|---|---|---|---|---|---|---|---|
| 20 | 245° C. | 9.9 g | 6.8 g | 0.3 g | 98% | 40% | 3.5 M/h |
| 21 | 230° C. | 11.2 g | 5.3 g | 0.6 g | 96% | 31% | 3.5 M/h |
| 22 | 215° C. | 5.6 g | 2.0 g | 0.7 g | 92% | 24% | 1.7 M/h |

[7]Other oxygenated liquid products.

EXAMPLES 23-24

These examples demonstrate the use of tetra-n-butyl-phosphonium bromide as a solvent and as a halide source, or as both in the practice of the process of the invention.

TABLE 4

| Example | 23 | 24 |
|---|---|---|
| Catalyst | $Ru_3(CO)_{12}$ | $Ru_3(CO)_{12}$ |
| mmol | 4.7 | 4.7 |
| solvent | p(n-Bu)$_4$Br | DMEU[10] |
| mL | 38 | 38 |
| Additive | Co/P(n-Bu)$_4$Br/o-PhDA[8] | Co/P(n-Bu)$_4$/o-PhDA |
| mmole | 7.0/118/93 | 7.0/59/93 |
| pres.,psi | 4000 | 4000 |
| Temp., °C. | 230 | 230 |
| Time,hrs. | 1.5 | 1.5 |
| $H_2$/CO | 1.0 | 1.0 |
| MeOH, g | 3.1 | 4.0 |
| EtOH, g | 3.5 | 3.1 |
| n-PrOH, g | 2.6 | 2.0 |
| n-BuOH, g | 0.7 | 0.4 |
| Acetates | 0.5 | 1.2 |
| Tot.Prod., g | 10.4 | 10.7 |
| Rate, total, M/h | 3.0 M/Kg-h[9] | 4.3 |
| $C_{2+}$alcohols % | 56(23% $C_{3+}$) | 43(16% $C_{3+}$) |

[8]o-phenylenediamine
[9]Rate expressed in moles of products per kilogram of P(n-Bu)$_4$Br
[10]1,3-dimethylethyleneurea

EXAMPLES 25-28

These examples demonstrate the use of rhodium (as rhodium carbonyl) as an additional component of the catalyst system.

TABLE 5

| Example | 25 | 26 | 27 | 28 |
|---|---|---|---|---|
| Catalyst | $Ru_3(CO)_{12}$ | $Ru_3(CO)_{12}$ | $Ru_3(CO)_{12}$ | $Ru_3(CO)_{12}$ |
| mmol | 4.7 | 4.7 | 4.7 | 4.7 |
| solvent | 1,3-DMEU | 1,3-DMEU | 1,3-DMEU | 1,3-DMEU |
| mL | 38 | 38 | 38 | 38 |
| Additive | Co/Rh/LiI/3,4-DAT[11] | Co/Rh/LiI/3,4-DAT | Co/Rh/LiI/3,4-DAT | Co/Rh/LiI/3,4-DAT |
| mmole | 4.4/0.5/30/93 | 7.0/1.0/30/93 | 7.0/1.0/30/93 | 7.0/1.0/30/93 |
| pres.,psi | 5000 | 5000 | 5000 | 5000 |
| Temp., °C. | 230 | 230 | 230 | 230 |
| Time,hrs. | 1.5 | 1.5 | 1.5 | 3.0 |
| $H_2$CO | 1.0 | 1.0 | 1.0 | 1.0 |
| MeOH, g | 7.3 | 5.9 | 5.6 | 4.9 |
| EtOH, g | 5.8 | 6.5 | 5.7 | 10.2 |
| n-PrOH, g | 0.5 | 1.0 | 0.9 | 2.1 |
| n-BuOH, g | 0.3 | 0.6 | 0.4 | 1.6 |
| Acetates | 0.5 | 0.9 | 0.9 | 2.3 |
| Tot. Prod., g | 14.4 | 13.9 | 13.5 | 21.1 |
| Rate, total, M/h | 6.5 | 6.3 | 5.9 | 4.04 |
| C2 + alcohols % | 37(3.5% $C_{3+}$) | 46(7% $C_{3+}$) | 43(6% $C_{3+}$) | 61(12% $C_{3+}$) |

[11]3,4-diaminotoluene

In the above, the term "Rate," unless otherwise indicated, means the rate of production of alcohols expressed in terms of number of moles of products per liter of catalyst solution per hour of reaction time.

We claim:

1. A liquid phase process for the selective manufacture of $C_{2+}$ alkanols wherein the yield of ethanol is greater than the yield of any of the other $C_{2+}$ alkanol products, said process being effected in a homogeneous liquid phase reaction mixture and consisting essentially of the reaction of hydrogen with carbon monoxide in the presence of methanol which is produced in situ directly from the reaction of hydrogen with carbon monoxide, and a catalyst containing ruthenium and cobalt in the form of carbonyl complexes, a halogen compound containing at least one of chlorine, bromine or iodine, and an aromatic compound which possess the structure $$=C-N\diagup_{\diagdown}$$
$$|$$
$$=C-N\diagup_{\diagdown}$$

wherein the carbon atoms form part of an aromatic ring and the double bonds represent aromatic unsaturation, and the nitrogen and its free valences constitute part of any group capable of forming an imidazole ring structure under the conditions of the syngas and homologation reactions or constitute part of an imidazole ring structure; said aromatic compound being soluble in said homogeneous liquid phase reaction mixture; and wherein said reaction is conducted at a pressure in the range of about 500 pounds per square inch to about 20,000 pounds per square inch and at a temperature in the range of about 100° C. to about 450° C.

2. A process as defined in claim 1, wherein rhodium is provided to the reaction.

3. A process as defined in claim 1, wherein the halogen compound and the aromatic compound are the same.

4. The process of claim 1 carried out continuously.

5. A process as defined in claim 1, wherein the aromatic compound is ortho-phenylenediamine.

6. A process as defined in claim 1, wherein the aromatic compound is 3,4-diaminotoluene.

7. A process as defined in claim 2, wherein the rhodium is in the form of a carbonyl complex.

* * * * *